(12) United States Patent
Dahmen et al.

(10) Patent No.: US 7,880,036 B2
(45) Date of Patent: Feb. 1, 2011

(54) PRODUCTION METHOD FOR ETHYLENEAMINE MIXTURES

(75) Inventors: Kirsten Dahmen, Freinsheim (DE); Alfred Oftring, Bad Dürkheim (DE); Katrin Baumann, Mannheim (DE); Randolf Hugo, Dirmstein (DE); Thilo Hahn, Kirchheimbolanden (DE); Johann-Peter Melder, Böhl-Iggelheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/529,087

(22) PCT Filed: Feb. 27, 2008

(86) PCT No.: PCT/EP2008/052337

§ 371 (c)(1),
(2), (4) Date: Aug. 28, 2009

(87) PCT Pub. No.: WO2008/104552

PCT Pub. Date: Sep. 4, 2008

(65) Prior Publication Data

US 2010/0099872 A1    Apr. 22, 2010

(30) Foreign Application Priority Data

Mar. 1, 2007   (EP) .................................. 07103297

(51) Int. Cl.
*C07C 209/48* (2006.01)
(52) U.S. Cl. ........................ 564/491; 564/490; 564/492; 544/358
(58) Field of Classification Search .................. None
See application file for complete search history.

(56) References Cited

U.S. PATENT DOCUMENTS

| | | |
|---|---|---|
| 2,429,876 A | 10/1947 | Gresham |
| 2,436,368 A | 2/1948 | Weber et al. |
| 3,255,248 A | 6/1966 | Suessenguth et al. |
| 3,462,493 A | 8/1969 | Coker et al. |
| 4,146,560 A | 3/1979 | Larkin et al. |
| 4,235,821 A | 11/1980 | Butte, Jr. et al. |
| 5,030,740 A | 7/1991 | Bowman et al. |
| 5,530,127 A | 6/1996 | Reif et al. |
| 5,869,653 A | 2/1999 | Johnson |
| 6,469,211 B2 | 10/2002 | Ansmann et al. |
| 2002/0058842 A1 | 5/2002 | Ansmann et al. |
| 2006/0041170 A1 | 2/2006 | Jonas et al. |

FOREIGN PATENT DOCUMENTS

| | | |
|---|---|---|
| DE | 1154121 | 9/1963 |
| DE | 2755687 A1 | 8/1978 |
| DE | 3003729 A1 | 8/1980 |
| DE | 68911508 T2 | 3/1994 |
| EP | 0212986 A1 | 3/1987 |
| EP | 0222934 A1 | 5/1987 |
| EP | 0382508 A2 | 8/1990 |
| EP | 0696572 A1 | 2/1996 |
| EP | 0913388 A1 | 5/1999 |
| EP | 0963975 A1 | 12/1999 |
| EP | 1209146 A1 | 5/2002 |
| EP | 1742045 A1 | 1/2007 |
| JP | 2002338536 A | 11/2002 |

OTHER PUBLICATIONS

Nishimura, Shigeo, "Handbook of Heterogeneous Catalytic Hydrogenation for Organic Synthesis", (2001) pp. 213-215.
Malveda, Michael P., "CEH Product Review: Ethyleneamines"; SRI Report, SRI International, (2003), pp. 1-53.
Gamage, Swarna A., et al., "Dicationic Bis(9-methylphenazine-1-carboxamides): Relationships between Biological Activity and Linker Chain Structure for a Series of Potent Topoisomerase Targeted Anticancer Drugs", J. Med., Chem, (2001), vol. 44, pp. 1407-1415.
U.S. Appl. No. 12/529,101, filed Aug. 28, 2009.
U.S. Appl. No. 12/529,096, filed Aug. 28, 2009.
U.S. Appl. No. 12/529,034, filed Aug. 28, 2009.
U.S. Appl. No. 12/529,047, filed Aug. 28, 2009.
U.S. Appl. No. 12/529,072, filed Aug. 28, 2009.
U.S. Appl. No. 12/529,079, filed Aug. 28, 2009.
U.S. Appl. No. 12/529,107, filed Aug. 28, 2009.

*Primary Examiner*—Brian J Davis
(74) *Attorney, Agent, or Firm*—Connolly Bove Lodge & Hutz LLP

(57) ABSTRACT

The invention relates to a process for preparing an ethylene amine mixture, which comprises hydrogenating an amino nitrile mixture comprising at least two α-amino nitriles in an amount of at least 5% by weight in each case in the presence of a catalyst and, if appropriate, a solvent.

18 Claims, No Drawings

PRODUCTION METHOD FOR ETHYLENEAMINE MIXTURES

CROSS-REFERENCE TO RELATED APPLICATIONS

This application is a national stage application (under 35 U.S.C. §371) of PCT/EP2008/052337, filed Feb. 27, 2008, which claims benefit of European application 07103297.3, filed Mar. 1, 2007.

BACKGROUND OF THE INVENTION

The invention relates to a process for preparing an ethylene amine mixture by hydrogenation of an amino nitrile mixture over a catalyst. The individual ethylene amines can, if appropriate, be isolated from the resulting ethylene amine mixture.

It is generally known that nitriles can be hydrogenated to the corresponding amines in the presence of catalysts. The known processes give the desired products, for example primary amines as main product and secondary and tertiary amines as by-products, as a function of the reaction parameters selected.

It is also known, in processes for preparing amines by hydrogenation of nitrites, that a certain amount of ammonia improves the selectivity of the hydrogenation to primary amines and suppresses the formation of secondary and tertiary amines. However, the hydrogenation in the presence of ammonia results in an additional engineering outlay associated with the separation from the product stream, the work-up and the possible recirculation of the ammonia. Furthermore, relatively high pressures can be necessary in the hydrogenation, since the partial pressure of ammonia has to be taken into account.

Thus, ethylenediamine (EDA), which is a starting material for, for example, the synthesis of complexing agents or bleaching activators which are used, inter alia, as detergent additives or additives to cleaners, can be produced as main product by hydrogenation of aminoacetonitrile (AAN). In an analogous way, the hydrogenation of iminodiacetonitrile (IDAN) gives diethylenetriamine (DETA) as main product. However, DETA or EDA are always formed as by-products in the hydrogenation of AAN or IDAN, respectively.

Numerous processes for the hydrogenation of the α-amino nitriles aminoacetonitrile (AAN) and iminodiacetonitrile (IDAN) or of β-amino nitrites are described in the prior art. It is known that the hydrogenation of β-amino nitrites generally proceeds without problems, while the hydrogenation of α-amino nitrites is associated with the occurrence of numerous disadvantages such as hydrogenolysis of the C—CN bond or the $R_2N$—C bond. "Handbook of Heterogeneous Catalytic Hydrogenation for Organic Synthesis, pp. 213-215" illustrates the problems encountered in the hydrogenation of α-amino nitriles for the example of α-alkylamino nitriles or cyclic α-amino nitrites compared to β-amino nitriles. The known stability problems of α-amino nitriles are presumably the main reason why up to the present day only the hydrogenation of the α-amino nitriles AAN and IDAN to EDA (ethylenediamine) and DETA (diethylenetriamine), respectively, has been described in detail. However, EDA and DETA are prepared industrially by the EDC and MEA processes described below. In the case of higher α-amino nitriles, however, a corresponding hydrogenation is not known.

DE-A 3 003 729 describes a process for the hydrogenation of aliphatic nitriles, alkyleneoxy nitriles and alkyleneamino nitriles to primary amines over a cobalt or ruthenium catalyst in the presence of a solvent system. The solvent system used comprises water and ammonia together with an ether or polyether. The alkyleneamino nitriles or alkyleneoxy nitriles which can be used as starting materials are in each case defined by means of complex general formulae. As specific compounds or examples which can be hydrogenated to the corresponding diamine, mention is made of, inter alia, ethylenediaminedipropionitrile (EDDPN; also referred to as N,N'-bis(cyanoethyl)ethylenediamine) or 3,3'-(ethylenedioxy) dipropionitrile. On the other hand, DE-A 3 003 729 discloses no pointer to the use of individual compounds such as AAN or EDA derivatives having cyanomethyl substituents, e.g. ethylenediaminediacetonitrile (EDDN) or ethylenediaminemonoacetonitrile (EDMN). In addition, the tatter does not come under the general definition of alkyleneamino nitriles according to this document.

EP-A 0 382 508 describes a process for the batchwise preparation of acyclic, aliphatic polyamines by hydrogenation of acyclic, aliphatic polynitriles in the liquid phase over Raney cobalt catalysts, preferably in the presence of anhydrous ammonia. Here, a polynitrile solution is fed into a reaction zone which comprises the Raney cobalt catalyst in an essentially oxygen-free atmosphere. During the entire reaction time, the polynitrile solution is fed in at a rate which is no greater than the maximum rate at which the polynitrile reacts with the hydrogen in the reaction zone. Further mention is made of a reaction parameter K which is suitable for determining the volume feed rate. The process described is restricted to the preparation of polyamines from polynitriles such as iminodiacetonitrile (IDAN), nitrilotriacetonitrile (NTAN) or further compounds having 2 or more cyano groups. However, the reaction of compounds having one cyano group, e.g. AAN to form EDA, is not described.

EP-A 212 986 relates to a further process in which aliphatic polynitriles can be hydrogenated in the presence of a liquid primary or secondary amine comprised in the feed stream over a granular Raney cobalt catalyst to form the corresponding polyamines. Mention is made of, inter alia, the amino component EDA which has to be present and also numerous further primary or secondary amines. This document also specifically states that IDAN can be hydrogenated to DETA.

DE-A 1 154 121 relates to a process for preparing ethylenediamine, in which the starting materials hydrocyanic acid, formaldehyde, ammonia and hydrogen are reacted in the presence of a catalyst in a one-pot process. Both the ammonia and the hydrogen are used in a molar excess over the further reactants hydrocyanic acid and formaldehyde which are present in equimolar amounts. In this process, the AAN formed in situ is therefore not isolated but is directly reacted further with hydrogen. A disadvantage of this process is that the desired product (EDA) is obtained relatively unselectively in small amounts.

U.S. Pat. No. 3,255,248 describes a process for the hydrogenation of organic nitrogen-carbon compounds which preferably have nitro, N-nitroso, isonitroso, cyano or aromatic-substituted amino groups to the corresponding amines in the liquid phase using a sintered catalyst comprising cobalt or nickel. Here, the starting material is sprinkled down either alone or in the presence of a solvent, for example water, tetrahydrofuran, methanol, ammonia or the reaction product formed, together with the hydrogen onto the catalyst. If compounds which are unsaturated on the nitrogen atom, e.g. cyano groups, are hydrogenated, the presence of ammonia in the reaction is recommended. This is made clear in example 1 of this patent where aminoacetonitrile is sprinkled down in the from of an aqueous solution together with liquid ammonia but without another solvent onto the sintered catalyst.

EP-A 1 209 146 relates to a further process for the continuous hydrogenation of nitriles to primary amines, in which the respective nitriles are hydrogenated in the liquid phase over a suspended, activated Raney catalyst based on an alloy of aluminum and the reaction is carried out in the absence of ammonia and basic alkali metal or alkaline earth metal compounds. Nitriles which can be converted into the corresponding ethylene amines are, among many others, AAN, IDAN, EDTN, EDDPN or ethylenediaminemonopropionitrile (EDMPN).

EP-B 0 913 388 relates to a process for the catalytic hydrogenation of nitriles, which comprises contacting of the nitrile with hydrogen in the presence of a cobalt sponge catalyst under conditions for carrying out the conversion of the nitrite group into the primary amine. The cobalt sponge catalyst has been treated beforehand with a catalytic amount of lithium hydroxide and the process is carried out in the presence of water. Suitable nitrites are aliphatic nitriles having from 1 to 30 carbon atoms, including β-amino nitriles such as dimethylaminopropionitrile. A further process for preparing polyamines from the corresponding polynitriles is disclosed in DE-A 27 55 687. In this process, the hydrogenation is carried out over a hydrogenation catalyst in pellet form in the presence of a stabilizer which inhibits decomposition of the catalyst. As polynitrile, it is possible to use, inter alia, ethylenediaminedipropionitrile (EDDPN). A suitable stabilizer is, inter alia, EDA.

US-A 2006/0041170 relates to a process for preparing TETA, in particular TETA salts, and their use as drugs. In this multistage process, EDDN is prepared first. EDDN is subsequently reacted with benzaldehyde to form a (cyclic) imidazolidine derivative. This cyclic compound, which has two cyano groups, is reduced, for example by reaction with hydrogen, to give the corresponding cyclic diamino compound. This diamino compound is in turn hydrolyzed in the presence of an acid to give the corresponding TETA salt. In an alternative embodiment, the cyclic diamino compound is likewise reacted with benzaldehyde to form the corresponding diimino compound which is subsequently again hydrolyzed in the presence of an acid to give the corresponding TETA salt. A further process alternative described in this document is reaction of EDDN with Boc protective groups (tert-butoxycarbonyl groups). The EDDN derivative protected by two Boc protective groups obtained in this way is subsequently hydrogenated to give the corresponding protected TETA derivative. The Boo protective groups are removed by acid hydrolysis to give the corresponding TETA salt. A disadvantage of this process described in US-A 2006/0041170 is, in particular, that it is a multistage hydrogenation process in which the starting material EDDN used firstly has to be chemically converted into a derivative in order to carry out the hydrogenation. A further disadvantage is that TETA is initially obtained as salt and not in the free base form.

The preparation of higher ethylene amines such as triethylenetetramine (TETA) or tetraethylenepentamine (TEPA) by direct hydrogenation of the corresponding α-amino nitriles has not yet been described. Higher ethylene amines such as TETA or TEPA are prepared (industrially) by other processes.

EP-A 222 934 relates to a process for preparing higher alkylene polyamines by reaction of a vicinal dihaloalkane with an excess of ammonia in the aqueous phase with addition of a strong base, resulting in formation of an imine intermediate which is subsequently reacted with an alkylene polyamine to form the higher alkylene polyamine. A suitable vicinal dihaloalkane is, in particular, ethylene dichloride (EDC or 1,2-dichloroethane). Alkylene polyamines used are, in particular, ethylenediamine or higher ethylene amines such as DETA and also TETA and TEPA. In these processes (EDC processes), a mixture of various ethylene amines (linear ethylene amines such as EDA, DETA, TETA, TEPA or higher ethylene amines and cyclic derivatives such as piperazine (Pip) or aminoethylpiperazine (AEPip)) is obtained. Depending on which ethylene amine is added to the starting materials EDC and $NH_3$, the reaction mixture comprises a corresponding proportion of higher ethylene amines. If, for example, TEPA is to be specifically produced, the ethylene amine TETA is added to the starting materials EDC and $NH_3$. As a result, the product (ethylene amine mixture) comprises a higher proportion of TEPA, but also the abovementioned further linear and cyclic ethylene amines. Disadvantages of this process are, in particular, that the process proceeds with a low selectivity (gives an ethylene amine mixture) and that a specific ethylene amine (for example DETA) firstly has to be prepared and is subsequently introduced into the process to produce the next higher ethylene amine (for example TETA) in a targeted manner or to increase the yield. However, this process presents a corrosion problem because of the starting materials used (haloalkanes) and the hydrochloric acid formed and also an environmental problem because of the salts formed.

U.S. Pat. No. 3,462,493 relates to a process for preparing TETA, in which an at least five-fold molar excess of EDA is reacted with ethylene dichloride or ethylene dibromide. By-products formed here are, in particular, Pip or piperazinoethylethylenediamine.

DE-T 689 11 508 describes an alternative process for preparing linearly extended polyalkylene polyamines such as TETA. In this process, a bifunctional aliphatic alcohol is reacted with an amine reactant in the presence of a tungsten-comprising catalyst. A suitable bifunctional aliphatic alcohol is, in particular, monoethanolamine (MEA), and EDA or DETA can, for example, be used as amine reactants. This process gives principally mixtures of linearly extended polyalkylene polyamines (i.e. ethylene amine mixtures). These ethylene amine mixtures comprise the ethylene amines DETA, TETA, TEPA, Pip, AEPip or piperazine derivatives of higher ethylene amines, with the proportion of the respective components varying as a function of the amine reactants used. If DETA is used as amine reactant, an ethylene amine mixture having a high proportion of TETA and TEPA is obtained. Disadvantages of this process are that the process proceeds with a low selectivity (in respect of the components of the ethylene amine mixture obtained) and that an additional ethylene amine has to be synthesized first and then reacted with the bifunctional aliphatic alcohol (for example MEA). This forms relatively large amounts of by-products such as aminoethylethanolamine (AEEA) or higher hydroxy-comprising ethylene amines which are of little commercial interest. The relatively large amount of by-product formed is due to MEA or the higher ethanolamines (e.g. AEEA) being able to react with themselves instead of with the amine used. Owing to the (statistically) many possible reactions, the selectivity to the linear TETA is quite low because of the coproducts and cannot be controlled. The synthesis can be carried out only at a partial conversion.

An overview of the preparation of ethylene amines is given by the SRI report "CEH Product Review Ethyleneamines", SRI International, 2003; pp. 1-53, in which EDA or DETA, in particular, are prepared by processes corresponding to those described above (using the starting materials EDC or MEA). Here, higher ethylene amines such as TETA or TEPA are formed as by-products or are obtained in higher yield by renewed reaction of the starting materials with EDA or DETA.

Thus, it is not disclosed anywhere in the prior art that mixtures of α-amino nitriles comprising, for example, AAN, IDAN, EDDN or other higher α-amino nitriles can also be hydrogenated. The processes according to the prior art are instead restricted to the hydrogenation of individual substances.

BRIEF SUMMARY OF THE INVENTION

It is therefore an object of the present invention to provide a simple and inexpensive process for preparing ethylene amines such as EDA, DETA, TETA, TEPA or Pip. It should achieve a high conversion at a high selectivity in each case, with the ratio of the ethylene amines being variable.

This object is achieved by a process for preparing an ethylene amine mixture, which comprises hydrogenating an amino nitrile mixture comprising at least two α-amino nitriles in an amount of at least 5% by weight in each case in the presence of a catalyst and, if appropriate, a solvent. For the purposes of the present invention, the term hydrogenation refers to the reaction of the amino nitrile mixture with hydrogen.

DETAILED DESCRIPTION OF THE INVENTION

For the purposes of the present invention, the term "α-amino nitrile" refers to any hydrocarbon-comprising compound which comprises at least one cyanomethylamino group (—NH—CH$_2$—CN). The α-amino nitrites preferably additionally comprise at least one ethylene group, a further cyano group and/or at least one further primary, secondary or tertiary amino group. AAN is likewise a preferred amino nitrite.

Preferred α-amino nitrites are selected from among aminoacetonitrile (AAN), iminodiacetonitrile (IDAN), ethylenediaminediacetonitrile (EDDN), ethylene-diaminemonoacetonitrile (EDMN), diethylenetriaminediacetonitrile (DETDN), diethylenetriaminemonoacetonitrile (DETMN), piperazinylethylaminoacetonitrite (PEAN), aminoethylpiperazinylacetonitrile (AEPAN) and cyanomethyl-piperazinylethylaminoacetonitrile (CMPEAN). Further α-amino nitriles which can be comprised in the amino nitrite mixture are, for example, nitrilotrisacetonitrile (NTAN) and diethylenetriaminetriacetonitrile (DETTN).

For the purposes of illustration, the chemical structural formulae of the above-mentioned amino nitriles are given below:

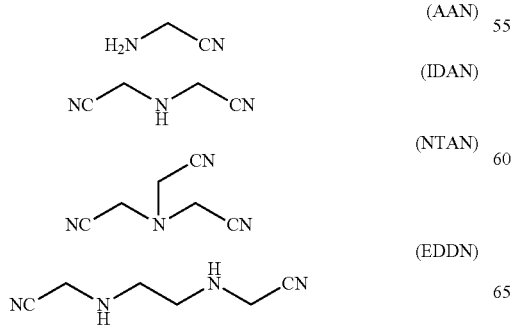

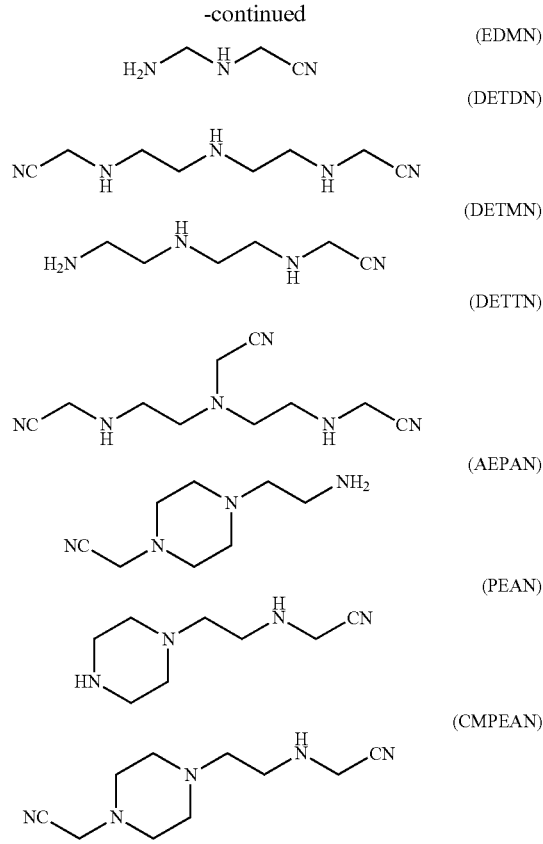

Particularly preferred α-amino nitriles are selected from among AAN, IDAN, EDDN, EDMN, DETDN or DETMN.

For the purposes of the present invention, the term "ethylene amine" refers to any hydrocarbon-comprising compound which comprises at least one ethylenediamine fragment (—NH—CH$_2$—CH$_2$—NH—). The ethylene amines preferably additionally comprise at least one further ethylene unit and a further primary, secondary or tertiary amino group. EDA is likewise a preferred ethylene amine. For the purposes of the present invention, ethylene amines include cyclic compounds such as piperazine (Pip) and derivatives thereof.

Ethylene amines which can be comprised as main product or by-product in the ethylene amine mixture in the process of the invention are selected from among

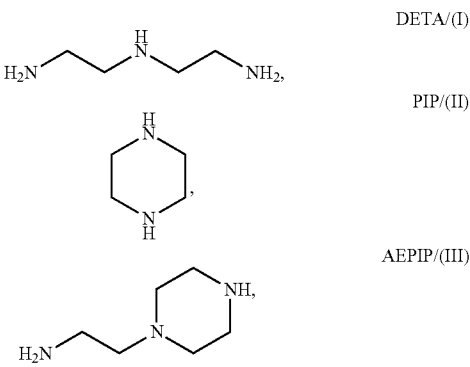

Preferred ethylene amines are selected from among ethylenediamine (EDA), diethylenetriamine (DETA), triethylenetetramine (TETA), tetraethylenepentamine (TEPA), pentaethylenehexamine (PEHA), piperazine (Pip) and aminoethylpiperazine (AEPip).

Particularly preferred ethylene amines are EDA, DETA, TEPA or TETA.

For the sake of completeness, it may be mentioned that, among the ethylene amines depicted above, the compound (VI) is referred to as piperazinoethylethylenediamine (PEEDA), the compound (VII) is referred to as diaminoethylpiperazine (DAEPip), the compound (X) is referred to as aminoethylpiperazinoethylethylenediamine (AEPEEDA) and the compound (XIII) is referred to as isopentaethylenehexamine (IPEHA).

The process of the invention has the advantage that linear ethylene amines, in particular EDA, DETA, TETA or TEPA, can be prepared with a high conversion and/or selectivity. The increased selectivity is indicated, in particular, by, for example, the MN used being hydrogenated predominantly to EDA or the EDDN used being hydrogenated predominantly to TETA. Compared to known processes for preparing TETA or TEPA, the desired main product (TETA or TEPA) can thus also be prepared in a targeted manner in high yield and with high selectivity. The by-products formed here can be further linear or cyclic ethylene amines. The proportion of cyclic ethylene amines is relatively low in the process of the invention. However, some of these by-products are also interesting products of value whose isolation is worthwhile, for example in industrial processes. In the process of the invention, appropriate formulation of an amine component and formaldehyde cyanohydrin or formaldehyde and hydrocyanic acid and also recirculation of some amine components enables the product mix to be matched to market requirements.

The α-amino nitriles used, e.g. AAN, IDAN or EDDN, are advantageously reacted completely or virtually completely. This is particularly important in the industrial processes since unreacted starting material is generally recirculated to the production circuit or has to be disposed of. Processes in which relatively large amounts of α-amino nitriles are not reacted are particularly disadvantageous because of the high instability of the α-amino nitrites. Firstly, AAN, IDAN and EDDN tend to decompose at elevated temperatures, so that the decomposition products can not be recirculated to the respective circuit, and secondly this decomposition can also proceed with explosive force. The hydrocyanic acid liberated in the decomposition can also significantly increase the catalyst consumption. Since the amino nitrites can be reacted completely in the process of the invention, no efforts have to be made to recirculate them into the production cycle.

A further advantage of the process of the invention is that, in contrast to EDC processes, it is not necessary to use chlorinated hydrocarbons as starting material. In addition, no hydrochloric acid or salts thereof are obtained as further reaction product. The disposal of the abovementioned materials is an (environmental) problem, particularly in industrial processes. An advantage over the MEA process is that, owing to the different starting materials, the formation of AEEA and further compounds having a hydroxy function does not play any role. Another advantage is that the process of the invention can be carried out continuously.

An advantage of being able to prepare an ethylene amine mixture instead of preparation of the individual components in separate campaigns or in separate processes is that the introduction of ammonia in the hydrogenation can be dispensed with. In the targeted preparation of ethylene amines according to the prior art, ammonia or other additives are generally added to suppress formation of secondary amines. In the synthesis according to the invention of ethylene amine mixtures, it is not necessary to suppress dimerization since dimers of the product mix are products of value. Thus, for example, the dimerization of EDA leads to DETA or that of EDA and TETA leads to TEPA.

Despite the fact that an ethylene amine mixture is in principle obtained in the process of the invention, the main components such as EDA, DETA, TETA or TEPA and, if appropriate, the further ethylene amines formed as by-products can be obtained by continuous isolation. In conventional processes in which the amino nitriles AAN or IDAN are in each case hydrogenated separately, DETA, EDA and further ethylene amines (in each case depending on the starting materials used) are always formed in principle as by-products. Accordingly, the same purification steps as in the process of the invention are generally necessary after the respective targeted ethylene amine syntheses in order to separate the by-products from the respective main product. Processes for separating off the by-products formed in the individual processes (for example DETA or EDA) therefore do not differ in principle from processes for isolating the main products formed in the process of the invention (e.g. EDA and DETA); only the amount of EDA or DETA to be separated off is different. In addition, when campaign operation is employed, only batchwise operation is possible, which is impractical because of the desired quantities. In the case of continuous operation, shutdowns and modifications of the plants have to be accepted (reduction of plant availability, necessity of cleaning, loss of product, personnel requirement, etc.). Appropriate storage capacities also have to be present to meet market requirements.

Another advantage is that, depending on market requirements, a higher or lower proportion of EDA, DETA, TETA or TEPA or the further ethylene amines in the ethylene amine mixture can be produced. The process of the invention is advantageously carried out continuously. This is due to the fact that the ratio of, for example, the starting material IDAN to AAN or EDDN to AAN is in principle reflected in the product in terms of the ratio of DETA to EDA or TETA to EDA. Thus, specific compositions of the amino nitrile mixture can be used in a targeted manner in the process of the invention in order to produce the ratios of quantities desired by the market.

The optimal operating conditions can be significantly different in the hydrogenation of individual amino nitriles. However, in the hydrogenation according to the invention of an amino nitrile mixture, the operating conditions to be set differ only slightly as a function of the composition and can therefore be optimized more easily. Thus, only a small degree of flexibility of the machines and apparatuses used is necessary, and this is normally present in commercially available equipment (e.g. output of pumps, operating temperature of heat exchangers, pressure design of apparatuses, etc.).

A further advantage of the hydrogenation according to the invention of amino nitrile mixtures, in particular those comprising AAN, over the separate preparation of, for example, DETA or, if appropriate, the further ethylene amines is the high complexity of the catalyst in the latter processes. The resulting product restriction has the consequence of a slower hydrogenation rate. In the preparation of EDA, the product restriction is significantly less, so that a higher hydrogenation rate of AAN is possible. If the hydrogenation of IDAN or, if appropriate, further amino nitriles is carried out in the presence of preferably at least 5% by weight of AAN as in the process of the invention, the product restriction of the corresponding ethylene amines is reduced. For a given amino nitrile mixture, the space-time yield of the respective component is therefore greater than in the corresponding hydrogenation of the individual components, or the hydrogenation of the mixture can be carried out at significantly lower pressures.

The process of the invention starts out from an amino nitrile mixture as starting material. The amino nitrile mixture comprises at least two α-amino nitriles, with at least two of these α-amino nitriles being comprised in the amino nitrile mixture in a proportion of at least 5% by weight. In the context of the process of the invention, amino nitrite mixtures therefore also include mixtures which comprise, for example, five different α-amino nitriles but only two of these α-amino nitriles are comprised in the amino nitrite mixture in proportions of at least 5% by weight while the other three α-amino nitriles can be comprised in proportions of less than 5% by weight. If appropriate, the amino nitrite mixture can additionally comprise further amino nitrites such as β-amino nitrites. The percentages by weight given both above and below in respect of the individual α-amino nitrites comprised in the amino nitrite mixture are based on the total amount of the α-amino nitrites comprised in the mixture. Any solvent present (water or organic solvent) or further additives are not taken into account in these figures. All amounts indicated are to be interpreted so that the sum of the α-amino nitrites comprised in the amino nitrite mixture does not exceed 100% by weight.

In a preferred embodiment of the present invention, the amino nitrile mixture comprises at least two α-amino nitrites which are each comprised in the amino nitrile mixture in a proportion of at least 10% by weight. In a further preferred embodiment, the amino nitrite mixture comprises at least two amino nitrites in proportions of at least 10% by weight and at least one further, preferably two further, amino nitrile(s) in a proportion of (in each case) at least 5% by weight. Furthermore, it is preferred that AAN is comprised in the amino nitrite mixture in a proportion of at least 5% by weight, preferably at least 10% by weight.

In an embodiment of the present invention, an amino nitrile mixture comprising at least two of the components a) to d), where
a) from 10 to 75% by weight of AAN,
b) from 10 to 50% by weight of IDAN, EDMN or a mixture thereof,
c) from 10 to 70% by weight of EDDN, DETMN or a mixture thereof,
d) from 5 to 50% by weight of DETDN and
e) from 0 to 10% by weight of PEAN, AEPAN, CMPEAN or a mixture thereof, is hydrogenated.

In further embodiments of the present invention, amino nitrite mixtures which comprise at least 5% by weight, preferably at least 30% by weight, of AAN and at least 5% by weight, preferably from 5 to 50% by weight, of IDAN are hydrogenated.

In further embodiments of the present invention, amino nitrite mixtures which comprise at least 5% by weight, preferably at least 30% by weight, of EDDN and at least 5% by weight, preferably from 5 to 50% by weight, of EDMN are hydrogenated.

In further embodiments of the present invention, amino nitrile mixtures which comprise at least 5% by weight, preferably at least 30% by weight, of DETDN and at least 5% by weight, preferably from 5 to 50% by weight, of DETMN are hydrogenated.

In general, any type/grade of the above-described α-amino nitriles, for example AAN, IDAN, EDMN, EDDN, DETMN or DETDN, can be used. If appropriate, the corresponding amino nitriles can also be used in the form of their aqueous or aqueous ammoniacal solutions. Processes for preparing, for example, AAN or IDAN are known to those skilled in the art. AAN and/or IDAN are preferably prepared by reaction of $NH_3$ and formaldehyde cyanohydrin (FACH).

Processes for preparing EDDN or EDMN are likewise known to those skilled in the art. Reference may here be made to K. Masuzawa et al., Bull. Chem. Soc. Japan, volume 41 (1968), pages 702-707; H. Brown et al., Helvetica Chimica Acta, volume 43 (1960), pages 659-666, and H. Baganz et al., Chem. Ber., 90 (1957), pages 2944-2949. EDDN and/or EDMN are preferably prepared by reaction of EDA and EACH. The molar ratio of EDA to FACH is preferably from 1:1.5 to 1:2. A novel process for preparing EDDN or mixtures comprising EDDN and EDMN has been filed by the applicant of the present invention at the same time.

DETDN and DETMN are new compounds which up to now have not been described in the literature. A process for preparing DETDN or mixtures comprising DETDN and DETMN has been filed by the applicant of the present invention at the same time.

DETDN is preferably prepared by reaction of DETA and FACH. The molar ratio of DETA to FACH is preferably from 1:1.5 to 1:2. The molar ratio of DETA to EACH is more preferably from 1:1.8 to 1:2. Processes for preparing DETA and FACH are known to those skilled in the art. In the process of the invention, DETA is preferably used in the form of the free base, but salts such as the dihydrochloride of DETA can also be used as starting material if appropriate. The preparation of DETDN is preferably carried out in a solvent, in particular in the presence of water. DETMN can be prepared by appropriately reducing the molar ratio of FACH to DETA compared to the preparation of DETDN, PEAN, AEPAN and CMPEAN are likewise new compounds which have up to now not been described in the literature. These three cyclic amino nitriles are obtained individually or as a mixture in the reaction of AEPip with FACH. The reaction conditions for the reaction of AEPip with FACH correspond in principle to the reaction conditions indicated above for the reaction of DETA with FACH. The molar ratio of AEPip to FACH is preferably from 1:1.5 to 1:2.

The individual α-amino nitriles comprising the amino nitrile mixture can in principle be synthesized separately from one another and combined in the appropriate amounts to form the amino nitrile mixture before use in the process of the invention. If appropriate, individual α-amino nitriles or all α-amino nitriles can also be synthesized together, for example AAN and IDAN, EDDN and EDMN or DETDN and DETMN. The concentrations obtained in the amino nitrile mixture as a result of the targeted use of the amine components can, if appropriate, be appropriately increased and/or decreased to the concentrations required by addition of the appropriate α-amino nitriles.

In an embodiment of the present invention, the hydrogenation products DETA, EDA and/or AEPip are recirculated in their entirety or in part. The recirculated hydrogenation products DETA, EDA and/or AEPip are reacted jointly or separately with FACH, preferably giving the α-amino nitriles DETDN and/or DETMN (recirculation of DETA), EDDN and/or EDMN (recirculation of EDA) or PEAN, AEPAN and/or CMPEAN (recirculation of AEPip). The α-amino nitriles prepared in this way are in turn fed to the hydrogenation. Which of the hydrogenation products DETA, EDA and/ or AEPip are recirculated to the circuit and the extent to which they are recirculated enables the respective proportion of the individual components of the ethylene amine mixture to be controlled.

In a further embodiment of the present invention, the low boilers are separated off from the amino nitrile mixture before the hydrogenation. If FACH is used for preparing the α-amino nitriles, the low boilers can be separated off before reaction of the FACH with $NH_3$, EDA, DETA or AEPip.

Hydrocyanic acid (HCN) is preferably separated off as low boiler. The separation is preferably effected by distillation, for example in the form of a thin film distillation such as a Sambay distillation ("Chemie Ingenieur Technik, Vol. 27, pages 257-261"). If appropriate, the reaction mixture can also be stripped by means of nitrogen. Furthermore, the concentration of water can be reduced, preferably by distillation, before hydrogenation of the amino nitrile mixture. Absorption of impurities on an absorbent, for example activated carbon or an ion exchanger, is likewise possible.

In embodiments of the process of the invention in which the amino nitrite mixture comprises less than 5% by weight of AAN, the hydrogenation is carried out in the presence of a solvent, for example an organic solvent and/or water. However, the (additional) use of an organic solvent (inert organic compound) and/or of water has been found to be advantageous since, in particular, stabilization of the individual components of the amino nitrile mixture, in particular in the presence of the resulting amines, can be achieved by use of an organic solvent. In addition, the use of solvents enables a flushing effect on the catalyst used to be achieved, as a result of which its operating life is increased or its consumption is reduced (longer catalyst life) and the space velocity over the catalyst can be improved.

A suitable solvent which can comprise one or more components should preferably have the following properties:
(a) the solvent should have a stabilizing effect on the components of the amino nitrile mixture, in particular reduce decomposition of AAN or IDAN at the prevailing temperatures;
(b) the solvent should display a good solvent capability for hydrogen;
(c) the solvent should be inert under the reaction conditions;
(d) the reaction mixture (amino nitrile mixture and solvent) should form a single phase under the reaction conditions;
(e) the choice of solvent should be made with a view to a preferred separation of the product from the product stream by distillation subsequent to the hydrogenation, preferably avoiding a separation which is energy-intensive or complicated in terms of apparatus (e.g. close-boiling mixtures or azeotropes which are difficult to separate);
(f) the solvent should readily be able to be separated off from the products, i.e. the boiling point should be sufficiently different from those of the products, with preference being given to a boiling point lower than those of the products.

Possible solvents are organic solvents, for example amides such as N-methylpyrrolidone (NMP) and dimethylformamide (DMF), aromatic and aliphatic hydrocarbons such as benzene and xylene, alcohols such as methanol, ethanol, propanol, isopropanol, butanol, isobutanol, secondary butanol and tertiary butanol, amines such as ethylene amines, alkylamines, ammonia, esters such as methyl acetate or ethyl acetate and ethers such as diisopropyl ether, diisobutyl ether, glycol dimethyl ether, diglycol dimethyl ether, dioxane and tetrahydrofuran (THF). Preference is given to using ethers, more preferably cyclic ethers and particularly preferably tetrahydrofuran, in the process of the invention. In a further preferred embodiment, alcohols, in particular methanol, are used as organic solvent.

The solvent is used in a weight ratio to the amino nitrile mixture used of from 0.1:1 to 15:1. The concentration of the amino nitrile mixture in the solution in which the hydrogenation is carried out should be selected so that a suitable feed rate or residence time can be set. Preference is given to mixing from 10 to 50% by weight of the amino nitrile mixture with the solvent. Based on the particularly preferred solvents methanol and tetrahydrofuran, it is advantageous, for example, to use the amino nitrile mixture in an amount of from 20 to 40% by weight based on the solvent.

If water is present, the proportion of water in the solution is in the range from 0 to 70% by weight, preferably from 10 to 50% by weight. The percentages indicated for the water are based on the amino nitrile/water mixture.

If appropriate, additional additives can be comprised in the solution in which the hydrogenation is carried out. Possible additives are in principle hydroxides such as alkali metal hydroxides, alkoxides, amides, amines and, if appropriate, ammonia. Preferred additives are amines such as EDA and ammonia, in particular EDA. Furthermore, acidic additives such as silicates can additionally be comprised in the solution. These substances can be added as pure substance or as a solution in a solvent. The process of the invention is preferably carried out with addition of additives as long as at least 5% by weight of EDDN, EDMN, DETDN or DETMN is comprised in the amino nitrile mixture.

In a preferred embodiment of the present invention, the hydrogenation of the amino nitrile mixture is carried out in the presence of EDA. To achieve a high selectivity and/or conversion to, for example, higher, in particular linear ethylene amines (e.g. TETA and/or TEPA), the hydrogenation of the corresponding amino nitrile mixture is carried out in the presence of EDA. The addition of further additives is not necessary, but they can likewise be added. If the corresponding amino nitrile mixture comprises AAN, no extra addition or recirculation of EDA is necessary because of the EDA formed in the hydrogenation.

In a further embodiment, the hydrogenation of an AAN-comprising amino nitrile mixture is carried out in the presence of ammonia which is dissolved in water and originates from the MN synthesis. This excess of ammonia can be transferred into the hydrogenation and separated off together with any ammonia formed by condensation reactions after the hydrogenation. The small amounts have no significant influence on the autogenous pressure in the system.

If ammonia is dissolved in the starting materials or in any aqueous solution used or is liberated as by-product in the hydrogenation, this does not interfere. Any ammonia present can be removed by methods known to those skilled in the art, for example by distillation.

As catalysts for the hydrogenation of the nitrile function to the amine, it is possible to use catalysts which comprise one or more elements of transition group 8 of the Periodic Table (Fe, Co, Ni, Ru, Rh, Pd, Os, Ir, Pt), preferably Fe, Co, Ni, Ru or Rh, particularly with Co or Ni, as active species. These include skeletal catalysts (also referred to as Raney® type; hereinafter also: Raney catalyst) which are obtained by leaching (activation) of an alloy of a hydrogenation-active metal and a further component (preferably Al). The catalysts can additionally comprise one or more promoters. In a preferred embodiment, Raney catalysts, preferably Raney cobalt or Raney nickel catalysts and particularly preferably Raney cobalt catalysts doped with at least one of the elements Cr, Ni or Fe or Raney nickel catalysts doped with one of the elements Mo, Cr or Fe are used in the process of the invention.

The catalysts can be used as all-active catalysts or in supported form. Supports used are preferably metal oxides such as $Al_2O_3$, $SiO_2$, $ZrO_2$, $TiO_2$, mixtures of metal oxides or carbon (activated carbons, carbon blacks, graphite).

The oxidic catalysts are activated outside the reactor or in the reactor by reduction of the metal oxides in a hydrogen-comprising gas stream at elevated temperature before use. If the catalysts are reduced outside the reactor, this can be followed by passivation by means of an oxygen-comprising gas stream or embedding in an inert material in order to avoid uncontrolled oxidation in air and to make safe handling possible. As inert material, it is possible to use organic solvents such as alcohols or else water or an amine, preferably the reaction product. The skeletal catalysts are an exception in the activation; these can be activated by leaching with aqueous base, as described, for example, in EP-A 1 209 146.

Depending on the process carried out (suspension hydrogenation, fluidized-bed process, fixed-bed hydrogenation), the catalysts are used as powder, crushed material or shaped bodies (preferably extrudates or pellets).

Particularly preferred fixed-bed catalysts are the all-active cobalt catalysts doped with Mn, P and alkali metal (Li, Na, K, Rb, Cs) which are disclosed in EP-A742 045. The catalytically active composition of these catalysts before reduction of hydrogen comprises from 55 to 98% by weight, in particular from 75 to 95% by weight, of cobalt, from 0.2 to 15% by weight of phosphorus, from 0.2 to 15% by weight of manganese and from 0.05 to 5% by weight of alkali metal, in particular sodium, in each case calculated as oxide.

Further suitable catalysts are the catalysts disclosed in EP-A 963 975, whose catalytically active composition before treatment with hydrogen comprises from 22 to 40% by weight of $ZrO_2$, from 1 to 30% by weight of oxygen-comprising compounds of copper, calculated as CuO, from 15 to 50% by weight of oxygen-comprising compounds of nickel, calculated as NiO, with the molar ratio of Ni:Cu being greater than 1, from 15 to 50% by weight of oxygen-comprising compounds of cobalt, calculated as CoO, from 0 to 10% by weight of oxygen-comprising compounds of aluminum and/or manganese, calculated as $Al_2O_3$ or $MnO_2$, and no oxygen-comprising compounds of molybdenum, for example the catalyst A disclosed in this document which has the composition 33% by weight of Zr, calculated as $ZrO_2$, 28% by weight of Ni, calculated as NiO, 11% by weight of Cu, calculated as CuO, and 28% by weight of Co, calculated as CoO.

Further suitable catalysts are the catalysts disclosed in EP-A 696 572 whose catalytically active composition before reduction of hydrogen comprises from 20 to 85% by weight of $ZrO_2$, from 1 to 30% by weight of oxygen-comprising compounds of copper, calculated as CuO, from 30 to 70% by weight of oxygen-comprising compounds of nickel, calculated as NiO, from 0.1 to 5% by weight of oxygen-comprising compounds of molybdenum, calculated as $MoO_3$, and from 0 to 10% by weight of oxygen-comprising compounds of aluminum and/or manganese, calculated as $Al_2O_3$ or $MnO_2$, for example the catalyst specifically disclosed in this document which has the composition 31.5% by weight of $ZrO_2$, 50% by weight of NiO, 17% by weight of CuO and 1.5% by weight of MoO$_3$. The catalysts described in WO-A 99/44984 which comprise (a) iron or a compound based on iron or mixtures thereof, (b) from 0.001 to 0.3% by weight, based on (a), of a promoter based on 2, 3, 4 or 5 elements selected from the group consisting of Al, Si, Zr, Ti, V, (c) from 0 to 0.3% by weight, based on (a), of a compound based on an alkali metal and/or alkaline earth metal and (d) from 0.001 to 1% by weight, based on (a) manganese are likewise suitable.

In suspension processes, preference is given to using Raney catalysts. In Raney catalysts, the active catalyst is produced as "metal sponge" from a binary alloy (nickel, iron, cobalt with aluminum or silicon) by leaching of one component by means of acid or alkali. Residues of the original alloying partner often act synergistically.

The Raney catalysts used in the process of the invention are preferably produced from an alloy of cobalt or nickel, particularly preferably cobalt, and a further alloying component which is soluble in alkalis. Aluminum is preferably used as this soluble alloying component, but it is also possible to use other components such as zinc and silicon or mixtures of such components.

To activate the Raney catalyst, the soluble alloying component is extracted completely or partly by means of alkali, for example aqueous sodium hydroxide. The catalyst then be washed, for example, with water or organic solvents.

One or more further elements can be present as promoters in the catalyst. Examples of promoters are metals of transition groups IB, VIB and/or VIII of the Periodic Table, e.g. chromium, iron, molybdenum, nickel, copper, etc.

The activation of the catalysts by leaching of the soluble component (typically aluminum) can be carried out either in the reactor itself or before introduction into the reactor. The preactivated catalysts are air-sensitive and pyrophoric and are therefore generally stored and handled under a medium such as water, an organic solvent or a substance which is present in the reaction carried out according to the invention (solvent, starting material, product) or embedded in an organic compound which is solid at room temperature.

Preference is given, according to the invention, to using a skeletal cobalt catalyst which has been obtained from a Co/Al alloy by leaching with aqueous alkali metal hydroxide solution, e.g. sodium hydroxide, and subsequent washing with water and preferably comprises at least one of the elements Fe, Ni, Cr as promoters.

Such catalysts typically comprise cobalt together with from 1 to 30% by weight of Al, preferably from 2 to 12% by weight of Al, very particularly preferably from 3 to 6% by weight of Al, from 0 to 10% by weight of Cr, preferably from 0.1 to 7% by weight of Cr, very particularly preferably from 0.5 to 5% by weight of Cr, in particular from 1.5 to 3.5% by weight of Cr, from 0 to 10% by weight of Fe, preferably from 0.1 to 3% by weight of Fe, very particularly preferably from 0.2 to 1% by weight of Fe, and/or from 0 to 10% by weight of Ni, preferably from 0.1 to 7% by weight of Ni, very particularly preferably from 0.5 to 5% by weight of Ni, in particular from 1 to 4% by weight of Ni, with the weights being based in each case on the total weight of the catalyst.

It can, for example, be advantageous to use a skeletal cobalt catalyst "Raney 2724" from W.R. Grace & Co. as catalyst in the process of the invention. This catalyst has the following composition:

Al: from 2 to 6% by weight, Co: $\geq$86% by weight, Fe: from 0 to 1% by weight, Ni: from 1 to 4% by weight, Cr: from 1.5 to 3.5% by weight.

According to the invention, it is likewise possible to use a skeletal nickel catalyst which has been obtained from an Ni/Al alloy by leaching with aqueous alkali metal hydroxide solution, e.g. sodium hydroxide, and subsequent washing with water and preferably comprises at least one of the elements Fe, Cr as promoters.

Such catalysts typically comprise nickel together with from 1 to 30% by weight of Al, preferably from 2 to 20% by weight of Al, very particularly preferably from 5 to 14% by weight of Al, from 0 to 10% by weight of Cr, preferably from 0.1 to 7% by weight of Cr, very particularly preferably from 1 to 4% by weight of Cr, and/or from 0 to 10% by weight of Fe, preferably from 0.1 to 7% by weight of Fe, very particularly preferably from 1 to 4% by weight of Fe, with the percentages by weight being based in each case on the total weight of the catalyst.

It can be advantageous to use, for example, a skeletal nickel catalyst A 4000 from Johnson Matthey as catalyst in the process of the invention.

This catalyst has the following composition:

Al: $\leq$14% by weight, Ni: $\geq$80% by weight, Fe: from 1 to 4% by weight, Cr: from 1 to 4% by weight.

When the activity and/or selectivity of the catalysts decreases, they can, if appropriate, be regenerated by methods known to those skilled in the art, as disclosed, for example, in WO 99/33561 and the documents cited therein.

The regeneration of the catalyst can be carried out in the actual reactor (in situ) or on the catalyst after removal from the reactor (ex situ). In fixed-bed processes, the catalyst is preferably regenerated in situ, while in the case of suspension processes, preference is given to continuously or discontinuously taking out part of the catalyst, regenerating it ex situ and returning it to the reactor.

The temperatures at which the process of the invention is carried out are in the range from 40 to 150° C., preferably from 80 to 140° C.

The pressure prevailing in the hydrogenation is generally from 5 to 300 bar, preferably from 30 to 250 bar, particularly preferably from 70 to 160 bar.

In a preferred embodiment, the amino nitrile mixture is fed into the hydrogenation at a rate which is no greater than the rate at which the amino nitrile mixture reacts with hydrogen in the hydrogenation.

The feed rate is thus preferably set so that an effectively quantitative conversion is achieved. This is influenced by temperature, pressure, type of mixture, amount and type of the catalyst, of the reaction medium, quality of mixing of the contents of the reactor, residence time, etc.

If a solvent is used in the process of the invention, the solvent can firstly be mixed completely with the amino nitrite mixture. The solution obtained, which can, if appropriate, also comprise additives, is subsequently fed into the reaction vessel comprising the catalyst. In continuous processes, a partial amount of the solvent can also be introduced into the reaction vessel separately from the solution which comprises the amino nitrile mixture and the solvent. In the embodiment of the process of the invention in which a mixture of AAN and at least one higher amino nitrile are used, completely separate introduction of the solvent is also conceivable. In a preferred embodiment, the amino nitrile mixture is introduced as an aqueous solution and the organic solvent is introduced separately.

In a preferred embodiment, the amino nitrite mixture comprised in the solution is fed in at a rate which is no greater than the rate at which the amino nitrile mixture reacts with hydrogen in the hydrogenation.

It is also possible, for example in semibatch processes, to place part of the solvent together with the catalyst in the reaction vessel and then feed in the solution.

The process of the invention for preparing ethylene amines by hydrogenation of amino nitrite mixtures can be carried out continuously, semicontinuously or batchwise in a fixed-bed, fluidized-bed or suspension mode in customary reaction vessels suitable for the catalysis. Suitable reaction vessels for carrying out the hydrogenation are ones in which contacting of the amino nitrile mixture and the catalyst with the gaseous hydrogen under superatmospheric pressure is possible.

The hydrogenation in the suspension mode can be carried out in a stirred reactor, jet loop reactor, jet nozzle reactor, bubble column reactor or in a cascade of identical or different reactors of this type. In the case of hydrogenation over a fixed-bed catalyst, tube reactors and shell-and-tube reactors are conceivable.

In the case of a fixed-bed catalyst, the amino nitrite mixture is passed over the catalyst in the upflow mode or downflow mode. However, preference is given to using the suspension mode in semicontinuous or preferably continuous operation.

The hydrogenation of the nitrile group takes place with liberation of heat which generally has to be removed. The removal of heat can be effected by means of built-in heat-exchange surfaces, cooling jackets or external heat exchangers in a circuit around the reactor. The hydrogenation reactor or a cascade of hydrogenation reactors can be operated in a single pass, As an alternative, it is also possible to employ a recycle mode of operation, in which part of the output from the reactor is recirculated to the reactor inlet, preferably without prior work-up of the recycle stream. Optimum dilution of the reaction solution can be achieved in this way. In particular, the recycle stream can be cooled in a simple and inexpensive way by means of an external heat exchanger and the heat of reaction can thus be removed. The reactor can be operated adiabatically in this way, with the temperature rise of the reaction solution being able to be limited by means of the cooled recycle stream. Since the reactor itself then does not have to be cooled, a simple and inexpensive construction is possible. An alternative is a cooled shell-and-tube reactor (only in the case of a fixed bed). A combination of the two modes of operation is also conceivable. Here, preference is given to installing a fixed-bed reactor downstream of a suspension reactor.

The process of the invention gives an ethylene amine mixture which comprises at least two ethylene amines, preferably at least two linear ethylene amines, as main component. The composition of the respective ethylene amine mixture depends strongly on the starting materials (α-amino nitriles) used. If, for example, an amino nitrite mixture comprising AAN and IDAN as main components is used, the ratio of the starting materials is in principle reflected after the hydrogenation in the corresponding products EDA and DETA. However, further DETA can be formed from AAN depending on the hydrogenation conditions. As a result, the proportion of DETA in the resulting amine mixture can increase by from 1 to 10% by weight. An analogous situation applies to mixtures which comprise more than 2 α-amino nitrites or further α-amino nitriles.

The ethylene amine mixture after the hydrogenation preferably comprises at least one ethylene amine, in particular at least two ethylene amines, selected from among ethylenediamine (EDA), diethylenetriamine (DETA), triethylenetetramine (TETA), tetraethylenepentamine (TEPA), pentaethylenehexamine (PEHA), piperazine (Pip), aminoethylpiperazine (AEPip), piperazinoethylethylenediamine (PEEDA) and diaminoethylpiperazine (DAEPip).

After the hydrogenation, the product obtained (ethylene amine mixture) can be purified further if appropriate, for example by separating off any solvent used and/or the catalyst by methods known to those skilled in the art. In particular, the main products (for example EDA, DETA, TETA or TEPA) can be isolated together or individually from the ethylene amine mixture by methods known to those skilled in the art. If the main products are isolated together, for example by means of distillation, they can subsequently be separated into the two individual products. Thus, pure EDA, pure DETA, pure TETA and pure TEPA is ultimately obtained. Other impurities or by-products such as cyclic ethylene amines (for example Pip) can likewise be separated off from the ethylene amine mixture by methods known to those skilled in the art. If appropriate, TETA can also be isolated together with the piperazine derivatives DAEPip and/or PEEDA as "technical-grade TETA".

As indicated above, amino nitrite mixtures comprising at least two of the components a) to e) in the respective concentrations indicated are hydrogenated in one embodiment of the present invention.

In a preferred embodiment, amino nitrile mixtures comprising the components a) to e) in the following amounts:
a) from 30 to 70% by weight, b) from 15 to 50% by weight, c) from 5 to 25% by weight and d) from 5 to 25% by weight, e) from 0 to 5% by weight, are hydrogenated.

The precise composition of the components a) to e) is determined by market requirements. Here, EDA is obtained as main component together with higher ethylene amines.

In a further preferred embodiment, TETA and TEPA are each obtained as main components. Here, EDA and DETA are prepared in parallel as building blocks necessary for any recirculation. This gives limits of
a) from 5 to 25% by weight, b) from 10 to 30% by weight, c) from 25 to 70% by weight and d) from 5 to 70% by weight, e) from 0 to 5% by weight.

However, further limits are also conceivable depending on the market.

In a preferred embodiment, the process of the invention is carried out using tetrahydrofuran or methanol as solvent. The temperature in the hydrogenation is preferably from 80 to 140° C., and the pressure is preferably from 30 to 250 bar. The hydrogenation is preferably carried out without introduction of additional ammonia.

The following examples illustrate the process of the invention. The proportions are in % by weight unless indicated otherwise. An internal standard, viz. diethylene glycol dimethyl ether (DEGDME), included in the process allows quantification of the product by determination of any volatile decomposition in products formed. Quantification is carried out by means of gas chromatography (GC), with methanol being added to the samples taken in each case in order to effect homogenization.

EXAMPLES

Formaldehyde Cyanohydrin 7000 g (70 mol) of formaldehyde (30%) are placed in a 6 l reaction vessel provided with a propeller stirrer and a pH of 5.5 is set by means of sodium hydroxide solution (1 mol/l).

1938 g (71.4 mol) of hydrocyanic acid are metered in gaseous form via a U-tube which has been heated to 50° C. and is located below the stirrer over a period of 3 hours, with the reaction temperature being maintained at 30° C. and the pH being maintained at 5.5. After a stirring time of 10 minutes, the pH is set to 2.5 by means of sulfuric acid (50% strength). To separate, off low boilers, in particular hydrocyanic acid, the reaction product mixture is subjected to a Sambay distillation (as described in "Chemie Ingenieur Technik, Vol. 27, pp. 257-261) (1 mbar, 30° C.). The respective content is determined by means of Liebig titration and set to a content of 43.6% of FACH by addition of water.

Example 1

An amino nitrile mixture is prepared from FACH, ammonia and FDA at 20 bar and 70° C. in an integrated laboratory plant comprising a tube reactor with preceding mixer and subsequent hydrogenation in an autoclave and is subsequently hydrogenated at 50 bar and 120° C. to form the corresponding ethylene amines. 137.3 g/h (1.05 mol/h) of FACH, 47.4 g/h (2.8 mol/h) of ammonia and 20.9 g/h (0.35 mol/h) of EDA, corresponding to a FACH:$NH_3$:EDA ratio of 3:5:1, are fed continuously into the tube reactor. The reaction product mixture comprises 9.5% by weight of AAN and 21% by weight of EDDN, which corresponds to a yield of AAN of 33% and of EDDN of 60%, based on FACH used. The total yield of amino nitriles is 93% with a total amino nitrile selectivity of 97%.

The reaction product mixture is mixed with an internal standard, viz. diethylene glycol dimethyl ether (DEGDME), at 20 bar without depressurization. 45 g/h of this mixture are hydrogenated continuously in the presence of 80 g/h of THF and 20 standard l of hydrogen at 50 bar and 120° C. in the presence of 10 g of Cr-doped Raney cobalt in a 270 ml autoclave provided with baffles and disk stirrer. The output from the hydrogenation is analyzed by means of GC. Amino nitriles can no longer be detected. In addition to 22% by weight of EDA, 0.7% by weight of Pip, 2.8% by weight of DETA and 16% by weight of AEPip and 41% of TETA are found.

Example 2

An amino nitrile mixture is prepared from FACH, ammonia and EDA at 20 bar and 70° C. in an integrated laboratory plant comprising a tube reactor with preceding mixer and subsequent hydrogenation in an autoclave and is subsequently hydrogenated at 50 bar and 120° C. to form the corresponding ethylene amines. 104.4 g/h (0.8 mol/h) of FACH, 22.6 g/h (1.3 mol/h) of ammonia and 15.9 g/h (0.26 mol/h) of EDA, corresponding to a FACH:$NH_3$:EDA ratio of 3:5:1, are fed continuously into two tube reactors connected in series. The reaction product mixture comprises 9.3% by weight of AAN, 0.3% by weight of IDAN and 21.5% by weight of EDDN, which corresponds to a yield of AAN of 30%, of EDDN of 56% and of IDAN of 1.2%, based on FACH used. The total yield of amino nitriles is 87% with a total amino nitrile selectivity of 87%.

The reaction product mixture is mixed with an internal standard, viz. diethylene glycol dimethyl ether (DEGDME), at 20 bar without depressurization. 45 g/h of this mixture are hydrogenated continuously in the presence of 80 g/h of THF and 20 standard l of hydrogen at 50 bar and 120° C. in the presence of 10 g of Cr-doped Raney cobalt in a 270 ml autoclave provided with baffles and disk stirrer. The output from the hydrogenation is analyzed by means of GC. Amino nitriles can no longer be detected. In addition to 24% by weight of EDA, 2% by weight of Pip, 7% by weight of DETA and 15% by weight of AEPip and 34% of TETA are found.

Example 3

Continuous Hydrogenation/30% by Weight of Water 10 g of Cr-doped Raney cobalt are placed in a 270 ml autoclave provided with baffles and disk stirrer and 50 standard l/h of hydrogen are continuously fed in. A mixture of 30 g/h of AAN, 9 g/h of water in 255 g/h of THF is pumped in continuously at 50 bar. Reaction mixture is discharged continuously via an immersed frit. The reaction temperature is maintained at 120° C. The output is depressurized via a regulating valve. Regular samples are analyzed by means of GC. At no time can AAN be detected in the output. The samples all show a selectivity of >98% of EDA and 1% of DETA.

24 g/h of AAN, 10 g/h of IDAN, 10 g/h of water and 255 g/h of THF are subsequently pumped in for 7 hours. Nitrile can no longer be detected in the GC analyses. Selectivities of 66% of EDA, 30% of DETA and 1% of piperazine are achieved here.

22.5 g/h of IDAN in 255 g/h of THF including 24 g/h of water in addition to 18 g/h of AAN (0.32 mol) are fed in for a further 7 hours. In this case, too, quantitative conversion of AAN and IDAN is obtained. The selectivities of the mixture are 41% of EDA, 51% of DETA and 3% of piperazine.

The invention claimed is:

1. A process for preparing an ethylene amine mixture which comprises hydrogenating an amino nitrite mixture comprising at least two α-amino nitriles in an amount of at least 5% by weight in each case in the presence of a catalyst and optionally a solvent.

2. The process according to claim 1, wherein the catalyst is a Raney catalyst.

3. The process according to claim 2, wherein the Raney catalyst is a Raney nickel catalyst or a Raney cobalt catalyst.

4. The process according to claim 1, wherein the hydrogenation is carried out in the presence of water or an organic solvent.

5. The process according to claim 4, wherein the organic solvent is tetrahydrofuran or methanol.

6. The process according to claim 1, wherein the α-amino nitrile is aminoacetonitrile (AAN), iminodiacetonitrile (IDAN), ethylenediaminediacetonitrile (EDDN), ethylenediaminemonoacetonitrile (EDMN), diethylenetriaminediacetonitrile (DETDN), diethylenetriaminemonoacetonitrile (DETMN), piperazinylethylaminoacetonitrile (PEAN), aminoethylpiperazinylacetonitrile (AEPAN) or cyanomethylpiperazinylethylaminoacetonitrile (CMPEAN).

7. The process according to claim 1, wherein the pressure is from 30 to 250 bar or the temperature is from 80° C. to 140° C.

8. The process according to claim 1, wherein the ethylene amine mixture comprises at least one ethylene amine selected from the group consisting of ethylenediamine (EDA), diethylenetriamine (DETA), triethylenetetramine (TETA), tetraethylenepentamine (TEPA), pentaethylenehexamine (PEHA), piperazine (Pip) and aminoethylpiperazine (AEPip).

9. The process according to claim 8, wherein one or more of the ethylene amines formed is/are isolated from the ethylene amine mixture.

10. The process according to claim 1, wherein the amino nitrile mixture is fed into the hydrogenation at a rate which is no greater than the rate at which the amino nitrile mixture reacts with hydrogen in the hydrogenation.

11. The process according to claim 1, wherein the α-amino nitriles comprised in the amino nitrile mixture are prepared by reaction of formaldehyde cyanohydrin (FACH) with $NH_3$, ethylenediamine (EDA), diethylenetriamine (DETA), or aminoethylpiperazine (AEPip).

12. The process according to claim 1, wherein ethylenediamine (EDA), diethylenetriamine (DETA), or aminoethylpiperazine (AEPip) produced in the hydrogenation is/are completely or partly recirculated in order to prepare α-amino nitriles comprised in the amino nitrile mixture.

13. The process according to claim 1, wherein low boilers are separated off from the amino nitrile mixture before the hydrogenation or formaldehyde cyanohydrin (FACH) from which the low boilers have been separated off is optionally used for the preparation of α-amino nitriles.

14. The process according to claim 6, wherein an amino nitrile mixture comprising at least two of the components a) to e) in the following amounts:
  a) from 10 to 75% by weight of AAN,
  b) from 10 to 50% by weight of IDAN, EDMN or a mixture thereof,
  c) from 10 to 70% by weight of EDDN, DETMN or a mixture thereof and
  d) from 5 to 50% by weight of DETDN, and
  e) from 0 to 10% by weight of PEAN, AEPAN, CMPEAN or a mixture thereof, is hydrogenated.

15. The process according to claim 3, wherein the hydrogenation is carried out in the presence of organic solvent and the organic solvent is tetrahydrofuran or methanol.

16. The process according to claim 15, wherein the α-amino nitrile is aminoacetonitrile (AAN), iminodiacetonitrile (IDAN), ethylenediaminediacetonitrile (EDDN), ethylenediaminemonoacetonitrile (EDMN), diethylenetriaminediacetonitrile (DETDN), diethylenetriaminemonoacetonitrile (DETMN), piperazinylethylaminoacetonitrile (PEAN), aminoethylpiperazinylacetonitrile (AEPAN) or cyanomethylpiperazinylethylaminoacetonitrile (CMPEAN).

17. The process according to claim 16, wherein the pressure is from 30 to 250 bar and the temperature is from 80° C. to 140° C.

18. The process according to claim 17, wherein the ethylene amine mixture comprises at least one ethylene amine selected from the group consisting of ethylenediamine (EDA), diethylenetriamine (DETA), triethylenetetramine (TETA), tetraethylenepentamine (TEPA), pentaethylenehexamine (PEHA), piperazine (Pip) and aminoethylpiperazine (AEPip).

* * * * *